United States Patent [19]

Parrone

[11] Patent Number: 4,875,491
[45] Date of Patent: Oct. 24, 1989

[54] CONDOM-HOLDER DEVICE

[76] Inventor: Tony Parrone, 3604 67th St., Kenosha, Wis. 53140

[21] Appl. No.: 172,284

[22] Filed: Mar. 23, 1988

[51] Int. Cl.⁴ .................................................. A61F 5/44
[52] U.S. Cl. .................................... 128/844; 206/69; 224/901; 604/349; 604/352
[58] Field of Search ............................ 604/347–353; 128/830, 842, 843, 844; 206/69, 813, 303, 398–402, 408; 224/901

[56] References Cited

U.S. PATENT DOCUMENTS

| 2,006,212 | 6/1935 | Grabler | 206/69 |
| 2,332,857 | 10/1943 | Karg | 206/69 |
| 3,136,417 | 6/1964 | Clinch | 128/844 |
| 3,282,414 | 11/1966 | Penksa | 128/844 |
| 3,536,066 | 10/1970 | Ludwig | 128/844 |
| 3,651,818 | 3/1972 | Vargo | 224/901 |
| 4,508,221 | 4/1985 | Olson | 206/813 |
| 4,638,790 | 1/1987 | Conway et al. | 128/844 |
| 4,738,357 | 4/1988 | Martin et al. | 604/349 |
| 4,741,434 | 5/1988 | Liebman | 206/69 |

FOREIGN PATENT DOCUMENTS

| 1158507 | 12/1983 | Canada | 604/349 |
| 0867582 | 2/1953 | Fed. Rep. of Germany | 604/349 |

Primary Examiner—C. Fred Rosenbaum
Assistant Examiner—Mario Costantino
Attorney, Agent, or Firm—Peter N. Jansson, Ltd.

[57] ABSTRACT

A condom-holder device including an unextended condom with a gathered annular wall portion, a condom mount for holding the unextended condom, and a device to secure the condom mount to the human body such that the condom may be reached and applied to the male organ with one hand without substantial interruption of activity.

7 Claims, 3 Drawing Sheets

CONDOM-HOLDER DEVICE

FIELD OF THE INVENTION

This invention is related generally to condoms for prophylactic and contraceptive use and, more specifically, to condom-holder devices for use immediately prior to intercourse.

BACKGROUND OF THE INVENTION

Condoms have been widely used since their invention in the 18th century. Condom use is easily understood and, as a result, condoms have played an important prophylactic and contraceptive role.

A problem or drawback with condoms, however, is that their use frequently involves a significant interruption in the pre-intercourse activity, that is, the foreplay activity between the male and female immediately prior to intercourse. Such interruption is caused by the need to open a condom package, a step typically carried out by tearing open a package with two hands, and then remove the condom from the package and apply it to the male organ.

The condom package may be inconveniently located when the need for it arises. Even when an unopened condom package is nearby, the package-opening and other steps required cause interruption and delay.

As a result of such interruption and delay, there is a break in attention of the male partner to the female, or vice versa depending on who is taking responsibility for condom use. Consequently, a prevailing favorable mood may erode. Furthermore, the interruption and delay draw attention to aspects of the proceedings which may be less than helpful to the intended attitude of the partners with respect to impending intercourse.

There is a clear need to overcome or reduce this negative aspect of condom use. There is a need for a condom-holder device which will facilitate the obtaining of a condom for application to male organ during the period just prior to intercourse.

OBJECTS OF THE INVENTION

It is an object of this invention to provide an improved condom-holder device overcoming some of the problems and shortcomings of the prior art.

Another object of this invention is to provide an improved condom-holder device facilitating the obtaining and applying of a condom during the period just prior to intercourse.

Another object of this invention is to provide an improved condom-holder device minimizing interruption of pre-intercourse activity.

Another object of this invention is to provide an improved condom-holder device which allows obtaining and applying a condom with one hand during pre-intercourse activity without a complete diversion of attention from normal pre-intercourse activity.

Another object of this invention is to provide an improved condom-holder device which allows preservation of a prevailing favorable mood prior to intercourse while allowing condom use.

These and other important objects will be apparent from the descriptions of this invention which follow.

SUMMARY OF THE INVENTION

This invention is an improved condom-holder device overcoming certain problems and shortcomings of the prior art, including those mentioned above. The condom-holder device of this invention is used for holding condoms of the type extendible to cover the male organ.

The invention has an unextended condom of the type with a gathered annular wall portion, a condom mount including means holding the unextended condom, and means to secure the condom mount to the human body within manual reach. With this invention, the unextended condom can easily be reached and applied to the male organ with one hand in a minimal amount of time and without substantial interruption of activity.

The gathered annular wall portion of the unextended condoms useful in this invention is either the typical coiled annulus of a condom or an accordion-like fold arrangement as hereafter described. However, a variety of other condoms may be used with and as part of this invention.

In several forms of this invention, the condom mount is annular and its holding means includes means to engage the gathered annular wall portion of the unextended condom.

In one particularly preferred embodiment, the condom mount includes a pair of layers forming an annular space between them which receives the gathered annular wall portion of a condom. At least one of the pair of layers forms a central opening. Both of the two layers preferably form central openings and such central openings are in axial alignment with each other. Most preferably, one of the aligned central openings is larger and the other is smaller.

In such embodiments, the gathered annular wall portion of the unextended condom is preferably a coiled annulus which is tucked into the annular space between the two layers of the device. The unextended condom also has an end portion extending across the central openings with the end portion at its edges being in contact with the layer which forms the larger opening.

In a highly preferred embodiment of the two-layered type just described, the layer which forms the smaller opening has means along its central opening to retain the coiled wall portion within the annular space during uncoiling. Such retention means is preferably an inward enlargement along the edge of such central opening. Such enlargement keeps the coiled annulus of a condom inside the annular space as the condom is uncoiled by insertion of the male organ through the central openings and into the condom.

Such condom mount may be attached to a waistband by means of a pair of straps, as hereafter described, which complete one embodiment of the condom-holder device of this invention. Such devices may be worn by either the male or the female. The condom holder of such device, when worn by the male, would preferably have the larger central opening against the male. When worn by the female, the smaller central opening would be against the female. Thus, in either case, during condom uncoiling for application to the male organ, with the condom supported in place in the condom mount, the edge around the smaller central opening (with any enlargement or other retention means along the edge) will be properly positioned to aid in retaining the condom until it is completely applied to the male organ.

After application of the condom to the male organ, the condom mount of this embodiment is preferably withdrawn. Or, depending on the preference of the user, the condom mount may be left in place.

Another embodiment of this invention of the type having an annular condom mount with a condom holding means engaging the gathered annular wall portion of the unextended condom is somewhat different. Such embodiment includes a condom mount which is a flat member having a central opening, and a holding means which includes adhesive on the flat member around the opening, the gathered annular wall portion being secured to the flat member around the opening by means of the adhesive. In this embodiment, the unextended condom preferably has a gathered annular wall portion with accordion-like folds.

In one particularly preferred form, the flat member has a break between aligned first and second ends which extends to the central opening. The adhesive securement of the unextended condom to the flat member preferably is non-permanent and serves to hold the first and second ends together, thus holding the annular flat member together. Thus, after application of the condom to the male organ the condom mount can be removed from the male organ without sliding along the length thereof.

In some of such embodiments, the flat member have first and second opposite surfaces with the unextended condom being on the first surface. A first removable cover is removably secured to the flat member over both the first surface and the unextended condom. A second removable cover is removably secured to the flat member over the second surface to cover the central opening, thus sealing the unextended condom within an enclosure prior to use of the condom-holder device.

In the most preferred forms of the embodiments just described, the means to secure the condom mount to the human body includes adhesive on the flat member, such adhesive being exposed by removal of one of the removable covers. Thus, this condom-holder device can be secured easily to the user in a position ready for easy relocation and use.

Yet another embodiment with an annular condom mount and a condom holding means which engages the gathered annular wall portion of the unextended condom differs significantly from those already described. In such embodiment, the condom mount includes a tubular member having first and second substantially circular edges, an outside surface, and at least one break formed by first and second removably engagable ends. The gathered annular wall portion of the unextended condom is stretched around the outside surface to hold the first and second ends in engagement. After application of the condom to the male organ, the condom mount can be removed from the male organ without sliding along the length thereof.

In another embodiment of this invention, the condom mount includes a first wall having inside and outside surfaces and a retaining means secured to the first wall and spaced therefrom to define a space which contains the unextended condom. The retaining means is preferably a second wall. The first and second walls preferably each have adjoining annular sealing edges such that the walls enclose the condom-containing space.

In such embodiments, the second wall is preferably removable from the first wall, preferably by tearing along scored lines or the like, to open the condom-containing space. Also, such embodiments preferably have adhesive on the outside surface of the first wall covered by a removable cover. When the cover is removed, the adhesive is exposed and the adhesive allows the device to adhere to the user, preferably the skin of the user, in a readily accessible position.

Various means may be used to secure the condom mount to the human body.

As already mentioned, the securing means in some cases preferably involves use of an adhesive on the condom mount such that the condom-holder device may adhere to the user, preferably the skin of the user, in a position ready for easy relocation and use, including in some cases easy withdrawal of the unextended condom.

In one preferred form, also previously mentioned, the means to secure the condom mount to the human body includes a body-encircling member with the condom mount being secured with respect to the body-encircling member. The body-encircling member is most preferably a waistband, with the condom mount secured with respect to the waistband by at least one elongated member extending from the waistband. The elongated member is preferably elastic such that the condom mount can readily be moved with respect to the body of the user without substantial movement of the waistband.

In such embodiments, there are most preferably a pair of the elongated members secured at their opposite ends with respect to the waistband. The condom mount is preferably attached between the elongated members, and the elongated members are preferably elastic. With this arrangement, the condom mount is drawn against the body of the user. And, it can readily be moved with respect to the body without substantial waistband movement.

As hereafter explained in greater detail, the exact manner of use of the various embodiments will vary to some extent depending on the details of such devices. However, in each case the device may be made ready and placed in a readily accessible position on the body of the user. This eliminates the need to seriously interrupt activities leading to coitus for the purpose of obtaining and opening a condom package prior to mounting on the male organ.

After or during foreplay, with the device of this invention already in a readily accessible position, the user may simply reach the device and take appropriate action with one hand.

With certain embodiments, the unextended condom may be withdrawn from the condom mount with one hand and applied with the same hand onto the male organ. With certain other embodiments, the condom mount and condom are reached with one hand and relocated to the end of the malee organ, and then drawn over the male organ as the condom extends in the normal manner. After such insertion is completed, the mount may either be left in place or it may be removed. Removal may either be back along the length of the male organ or, for those embodiments in which the annular mount is broken, by simple lateral removal.

DETAILED DESCRIPTIONS OF PREFERRED EMBODIMENTS

The figures illustrate four condom holder devices in accordance with preferred embodiments of this invention. These include: a condom-holder device 10 shown in FIGS. 1-3; another condom-holder device 12 shown in FIGS. 4 and 5; another device 14 shown in FIGS. 6 and 7; and still another device 16 shown in FIGS. 8 and 9.

Figure 1:
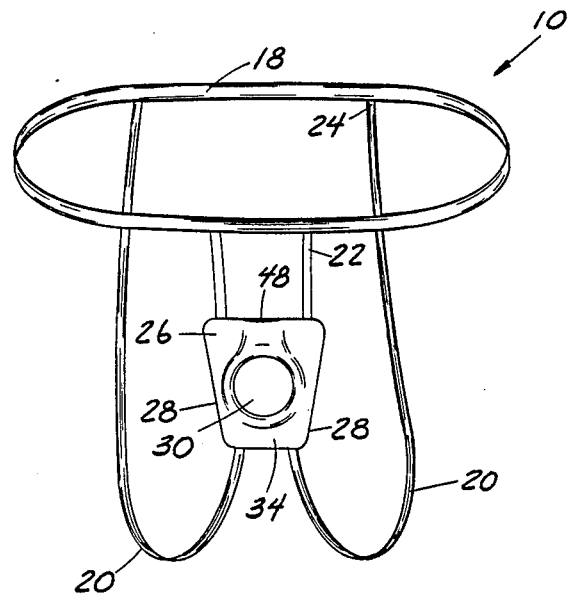
FIG. 1 is a perspective view of an improved condom-holder device in accordance with a preferred embodiment of this invention.
Figure 2:
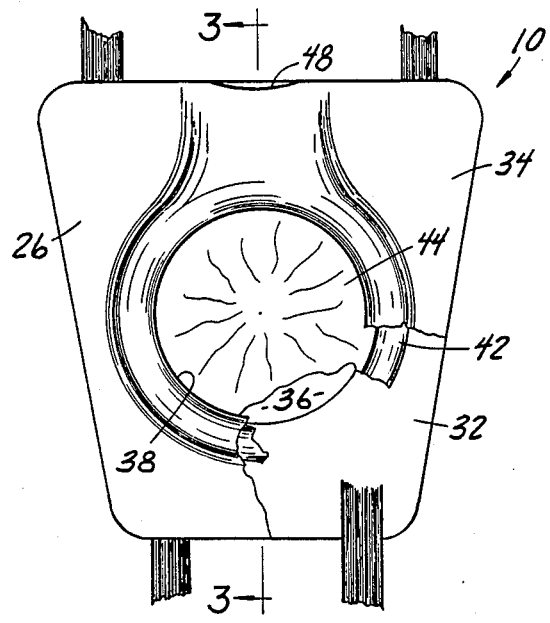
FIG. 2 is an enlarged fragmentary front view of FIG. 1, partially broken away to illustrate certain elements.

As shown best in FIG. 1, condom-holder device 10 includes an elastic waistband 18 and a pair of elongated elastic straps 20. Each elongated strap 20 has opposite ends 22 and 24 attached to waistband 18. Condom-holder device 10 also includes a condom mount 26 having opposite lateral edges 28 which are attached to elongated straps 20 such that condom mount 26 extends between straps 20.

An unextended condom 30 is held within condom mount 26. Condom mount 26 is annular and holds unextended condom 30 by engaging the gathered (coiled) annular wall portion 42 thereof in a manner hereafter described.

When condom-holder device 10 is worn, prior to intercourse, condom mount 26 is positioned against the stomach of the wearer, preferably just above the sexual organs. Waistband 18 and elongated straps 20 hold condom mount 26 against the stomach of the wearer while the elastic nature of elongated straps 20 allows condom mount 26 to be moved easily to a position over the sexual organs without substantial movement of waistband 18.

The condom mount 26 includes first and second layers 32 and 34 which are preferably flexible rubber sheets joined together in face-to-face fashion. First and second layers 32 and 34 form aligned first and second central openings 36 and 38. First and second openings 36 and 38 are different in size, first opening 36 being larger and second opening 38 being smaller.

The overlying central portions of first and second layers 32 and 34, that is, the portions immediately adjacent to the edges about openings 36 and 38, are not attached to one another. Thus, an annular space 40 is formed between first and second layers 32 and 34 near first and second central openings 36 and 38. Coiled annular portion 42 is sandwiched within annular space 40 to hold condom 30 in position ready for use.

Figure 3:
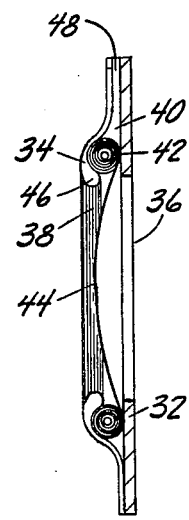
FIG. 3 is a right side sectional view taken along section 3—3 as indicated in FIG. 2.

Unextended condom 30 also includes an end portion 44 attached at its edges to coiled wall portion 42, actually integrally formed with wall portion 42. End portion 44 at its edges is in contact with first layer 32, immediately adjacent to first central opening 36, as illustrated in FIG. 3. An inward enlargement 46 extends along the edge forming second central opening 38. Enlargement 46, itself annular, serves to retain coiled annular wall portion 42 of condom 30 within annular space 40 during its uncoiling, as condom 30 is applied to the male organ.

Well prior to use of condom holder device 10, condom 30 may be inserted into annular space 40 in one of two ways. It either may be tucked into annular space 40 from positions around one of the central openings 36 and 38 or it may be slipped between first and second layers 32 and 34 by means of a top opening 48 along the upper edge of condom mount 26. Another possibility is that condom 30 is sold already placed within annular space 40 of a condom mount.

After condom 30 is assembled with condom mount 26, condom holder device 10 may be donned in the same manner as pants. This is done well prior to intercourse. Later, during the latter part of pre-intercourse activity, just prior to intercourse, the wearer of condom-holder device 10 simply grasps condom mount 26 in one hand and moves it to the male organ, applying both mount 26 and the condom on it onto the male organ until condom 30 is fully extended. At that point, condom mount 26 is preferably withdrawn along the length of the male organ and moved to a position out of the way, such as against the stomach of the wearer, where condom-holder device 10 was previously located.

Condom-holder device 10 may be worn by either the male or the female partner. When worn by the male, first layer 32 is preferably against the male; when worn by the female, second layer 34 is preferably against the female. In either case, condom mount 26 is oriented in the proper direction such that condom 30 is retained securely within annular space 40 during application to the male organ, that is, at least until such application is completed.

Figure 4:
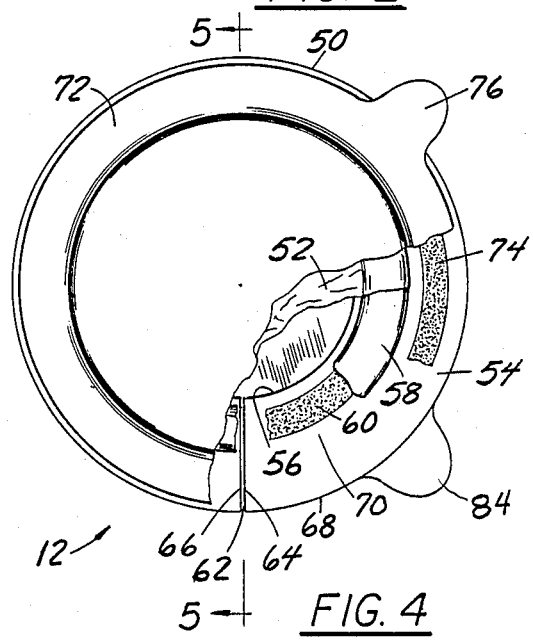
FIG. 4 is a front elevation of another embodiment of this invention.
Figure 5:
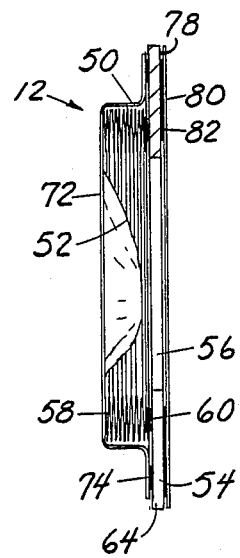
FIG. 5 is a right side sectional view taken along section 5—5 as indicated in FIG. 4.

FIGS. 4 and 5 illustrate a condom holder device 12 having another type of annular condom mount 50, a another type of unextended condom 52, and an adhesive means to secure condom mount 50 to the human body.

More specifically, condom mount 50 includes a flat member 54 having a central opening 56. Unextended condom 52 has an accordion-like gathered annular wall portion 58 made of many accordion-like folds. The end of the accordion-like folded portion 58 is secured to flat member 54 around central opening 56 by means of an adhesive layer 60. Adhesive layer 60 is a non-permanent adhesive such that condom 52 may be disconnected from flat member 54 when condom 52 is fully applied to the male organ.

Flat member 54 has a break 62 defined between first and second aligned ends 64 and 66. Break 62 extends from the radial outer edge 68 of flat member 54 all the way to central opening 56. The adhesive securement of unextended condom 52 to flat member 54, by means of adhesive layer 60, holds ends 64 and 66 in alignment. After application of condom 52 to the male organ, condom mount 50 may be removed from the male organ by spreading break 62. Using this technique, it is unnecessary to slide condom mount 50 along the length of the male organ for removal.

Condom 52 is attached to a first surface 70 of flat member 54, as already described. A first removable cover 72 is removably secured to first surface 70 of flat member 54 by an adhesive layer 74. First removable cover 72 covers both first surface 70 and unextended condom 52.

Adhesive layer 74 is a non-permanent adhesive such that first removable cover 72 may readily be peeled away from flat member 54 to expose unextended condom 52. Instead of an adhesive, a heat-sealing technique could be used to secure first removable cover 72 to first surface 70. First removable cover 72 has a tab 76 along its edge. Tab 76 facilitates the peeling away of cover 72 from flat member 54.

The surface of flat member 54 opposite first surface 70 is second surface 78. A second removable cover 80 is secured to second surface 78 by means of an adhesive layer 82. Adhesive layer 82 is a non-permanent adhesive with preferential adherence to second surface 78 rather than cover 80. Second removable cover 80 has a tab 84 along its edge to facilitate the peeling away of cover 80 from flat member 54. When second removable cover 80 is peeled away from flat member 54, adhesive layer 82 remains in place on flat member 54. Adhesive layer 82 is used to secure flat member 54 to the human body in a position within easy manual reach.

First and second removable covers 72 and 80 of condom-holder device 12 completely enclose and seal condom 52 prior to use. Thus, condom-holder device 12 serves as a package and as well as a device for ready accessibility immediately prior to intercourse.

In use, second removable cover 80 is removed well prior to intercourse and well prior to the acivity immediately prior to intercourse. Condom-holder device 12 is applied to the skin or underclothing of the user at a position within manual reach. First removable cover 72 may be removed either at this point or just prior to intercourse.

Immediately prior to intercourse, cover 72 is removed (if not previously removed) and the remaining portion of condom-holder device 12 is moved from the position of adherence to the position of application to the male organ. There is no need for two-handed opening of a condom package; this device may be opened and applied using only one hand, without serious interruption of pre-intercourse activity. The remaining steps of application and removal have already been described.

Figure 6:
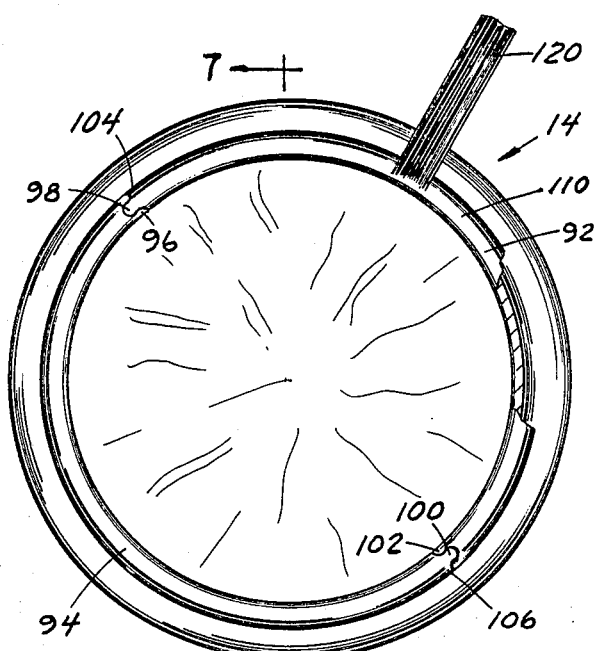
FIG. 6 is a a fragmentary rear elevation of another embodiment of this invention.
Figure 7:
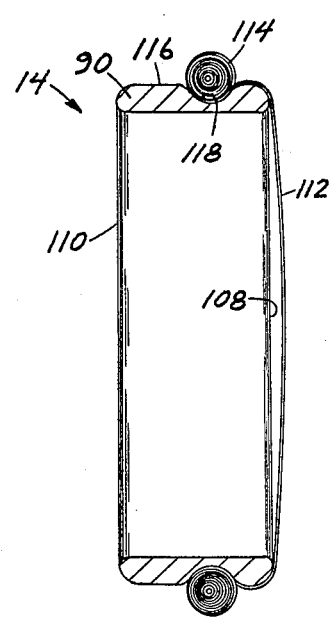
FIG. 7 is a right side sectional view taken along section 7—7 as indicated in FIG. 6.

FIGS. 6 and 7 show another embodiment of this invention having an annular condom mount. In this case, the annular condom mount is a tubular member 90 made of material having enough body and form that a substantially circular shape may be maintained at least while tubular member 90 is axially compressed. Tubular member 90 has first and second semi-cylindrical portions 92 and 94. First semi-cylindrical portion 92 has a first end 96 adjoining a first end 98 of second semi-cylindrical portion 94, and a second end 100 adjoining a second end 102 of second semi-cylindrical portion 94. First ends 96 and 98 are mating ends as are second ends 100 and 102. Between such pairs of ends, breaks 104 and 106 are formed in tubular member 90.

Tubular member 90 has first and second substantially circular edges 108 and 110. An unextended condom 112, more specifically, its coiled annular wall portion 114, is stretched around the outside surface 116 of tubular member 90, with condom 112 extending over first circular edge 108. Coiled wall portion 114 engages a shallow annular groove 118 formed on outside surface 116. Tubular member 90 is of sufficient size to loosely receive the male organ during intercourse; thus, coiled annular wall portion 114 of condom 112 is in tension around outside surface 116. Such tension serves to hold the adjoining ends of first and second semi-cylindrical portions 92 and 94 of tubular member 90 in engagement.

An elongated strap 120 is attached to tubular member 90 at a position along second circular edge 110. Strap 120 may itself be attached to a waistband like waistband 18 of FIG. 1, or a pair of elongated straps may be used. A variety of other securement means are possible.

In use, immediately prior to intercourse, tubular member 90 may be relocated to a position on the male organ and used for application of condom 112 to the male organ. After such application, with condom 112 off tubular member 90, first and second semi-cylindrical portions 92 and 94 may readily be separated such that tubular member 90 may be removed from the male organ without sliding along the length thereof.

Figure 8:
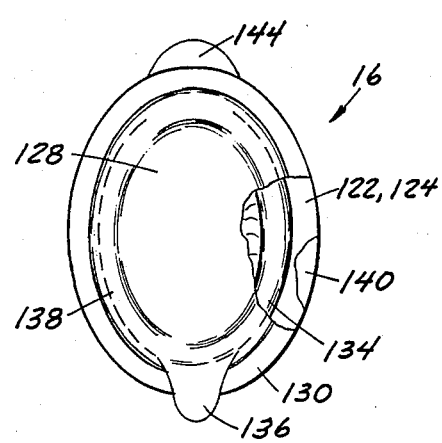
FIG. 8 is a front elevation of another embodiment of this invention.
Figure 9:
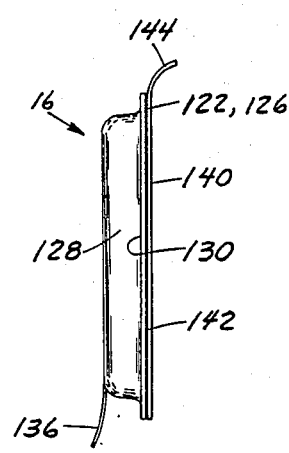
FIG. 9 is a right side elevation of FIG. 8.

As illustrated in FIGS. 8 and 9, condom-holder device 16 has a condom mount which includes a first wall 122 having inside and outside surfaces 124 and 126, and a second wall 128 secured to first wall 122. More specifically, first and second walls 122 and 128 are heat-sealed together along common annular edge portions 130. Second wall 128 is spaced from first wall 122 to define a space which contains unextended condom 134.

Attached to or formed as a part of second wall 128 is a tab 136. A portion of second wall 128 may be torn away from the condom mount of condom-holder device 16 by pulling on tab 136, score lines 138 being provided to facilitate such tearing.

A cover 140 is removably secured over outside surface 126 of first wall 122 by an adhesive layer 142. Adhesive 142 is a non-permanent adhesive which has preferential adherence for outside surface 126. Thus, when cover 140 is removed, condom-holder device 16 may be adhered to the user in an easily reachable position for subsequent use. Cover 140 includes a tab 144 which facilitates its removal.

In use, cover 140 is removed well prior to intercourse and the condom mount is adhered to the user in ready position. Later, immediately prior to intercourse, tab 136 is pulled to remove a portion of second wall 128, thus exposing condom 134. This operation and removal and application of condom 134 to the male organ may be carried out with one hand, without significant interruption of pre-intercurse activity.

A variety of materials may be used in making embodiments of this invention, including those illustrated in the drawings. Appropriate materials and manufacturing methods would be well known to those skilled in the art who are familiar with this invention.

While the principles of this invention have been described in connection with specific embodiments, it should be understood clearly that these descriptions are made only by way of example and are not intended to limit the scope of the invention.

I claim:

1. A condom-holder device of the type having a condom extendible to cover the male organ comprising:
   an unextended condom having a gathered annular portion;
   a pair of walls which define a space therebetween containing the unextended condom and have substantially aligned annular edges, at least a portion of one of the walls being removable from the other wall to open said condom-containing space;
   means attaching the aligned annular edges of the walls to enclose said space;
   body-securement adhesive along the aligned annular edges in position about said space for securement to the human body within manual reach; and
   means to removably cover said body-securment adhesive prior to securement to the human body, whereby the condom may be reached and applied to the male organ with one hand without substantial interruption of activity.

2. The comdon-holder device of claim 1 wherein:

the means attaching the aligned annular edges includes a flat annular member having a central opening and opposed first and second surfaces;

the first surface of said flat annular member has condom-securement adhesive thereon about the central opening, said condom-securement adhesive securing the gathered annular portion of the condom to the first surface of the flat member; and the body-securement adhesive is on the second surface of the flat member.

3. The condom-holder device of claim 2 wherein the means to removably cover said body-securement adhesive is one of said pair of walls, said one wall being secured to the second surface of the flat member.

4. The condom-holder device of claim 3 wherein the other of said pair of walls is removably secured to the first surface of said flat member over the unextended condom.

5. The condom-holder device of claim 3 wherein the gathered annular portion of the unextended condom has accordion-like folds.

6. The condom-holder device of claim 3 wherein:

the flat member has a break between first and second aligned ends which extends to the central opening; and the adhesive securement of the unextended condom to the flat member is non-permanent and holds the first and second ends together, whereby after application of the condom to the male organ the condom mount may be removed from the male organ without sliding along the length thereof.

7. A condom-holder device of the type having a condom extendible to cover the male organ comprising:

an unextended condom having a gathered annular portion;

a condom mount including first and second walls which define a space therebetween containing the unextended condom and have adjoining annular sealing edges enclosing said space, the first wall having inside and outside surfaces and at least a portion of the second wall being removable from the first wall to open said space;

adhesive on said outside surface to secure the condom mount to the human body within manual reach; and a cover removably secured to the outside surface such that removal thereof exposes the adhesive on said outside surface, whereby the condom may be reached and applied to the male organ with one hand without substantial interruption of activity.

* * * * *